United States Patent
Vossiek et al.

[11] Patent Number: 5,883,309
[45] Date of Patent: Mar. 16, 1999

[54] ADAPTIVE OPTIMIZATION PROCESS FOR ULTRASONIC MEASUREMENT SIGNALS

[75] Inventors: Martin Vossiek, München; Peter-Christian Eccardt, Ottobrunn, both of Germany

[73] Assignee: Siemens Aktiengesellschaft, Munich, Germany

[21] Appl. No.: 913,691
[22] PCT Filed: Feb. 23, 1996
[86] PCT No.: PCT/DE96/00304
    § 371 Date: Sep. 11, 1997
    § 102(e) Date: Sep. 11, 1997
[87] PCT Pub. No.: WO96/28259
    PCT Pub. Date: Sep. 19, 1996

[30] Foreign Application Priority Data

Mar. 15, 1995 [DE] Germany .................. 195 09 374.7

[51] Int. Cl.[6] ................................................. G01N 29/00
[52] U.S. Cl. ........................................... 73/602; 73/629
[58] Field of Search ........................ 73/602, 1.82, 632, 73/642, 629; 702/39, 103

[56] References Cited

U.S. PATENT DOCUMENTS 4,520,670  6/1985  Salomonsson et al. ............. 73/602
5,513,531  5/1996  Sapia et al. ........................ 73/602

FOREIGN PATENT DOCUMENTS

WO 96/01701  1/1996  WIPO.

OTHER PUBLICATIONS

"Erfahrungsaustausch Ultraschall–CS Technik," Crostack, *Fachberichte Hüttenpraxis Metallweiterverarbeitung*, vol. 19, No. Feb. (1981), pp. 113–123.

"Digital Preshaping of Ultrasonic Signals: Equipment and Applications," Börjesson et al., 1982 Ultrasonics Symposium, pp. 696–699.

"The Deconvolution Problem: An Overview," Riad, *IEEE* 1996 (4 pages).

"Optimization by Simulated Annealing," Kirkpatrick et al., *Science* vol. 220, No. 4598, May 13, 1983, pp. 671–680.

*Primary Examiner*—John E. Chapman
*Attorney, Agent, or Firm*—Hill & Simpson

[57] ABSTRACT

In order to optimize an ultrasound measurement signal application-specifically, an error value is formed from features with which an evaluation of the received ultrasound measurement signal is possible. An ultrasound signal, whose signal shape is modified by section-by-section variation of the shape of the transmission signal is emitted out, received and an error value is formed anew. This procedure is repeated until the error value assumes a minimum. The ultrasound measurement signal at which the error value is minimal corresponds to the optimized signal.

12 Claims, 7 Drawing Sheets

```
INITIALIZATION
-START- TRANSMISSION SIGNAL (WITH b BITS AMPLITUDE
RESOLUTION AND N SAMPLES)
S₀={S₀1,S₀2,...,S₀n,S₀n+1,...,S_N}={0,0,...,0,2^b,0,...,0}
ADAPTATION STEP WIDTH: FOR EX. d=2^{b-2}
OPERATIONAL SIGN OF ADAPTATION DIRECTION Vz=+1
```

| FOR ALL SAMPLE POINTS $s_{kn}$ $1 \le n \le N$ |
|---|
| AS LONG AS AN OPTIMIZATION WITH RESPECT TO AN INDIVIDUAL SAMPLE POINT $s_{kn}$ IS POSSIBLE |
| GENERATE TEST SIGNAL<br>S'=S_k+{0,0,...,s_{kn}'=s_{kn}+VZ·d,0,...,0} |
| SEND TEST SIGNAL S',<br>DETERMINE FEATURES,<br>CALCULATE $\zeta$ (S') |
| HAS RECEPTION SIGNAL IMPROVED?<br>$\zeta$ (S') < $\zeta$ (S_k) |

| Y | N |
|---|---|
| UPDATE TRANS. SIGNAL $S_k$ =S' | IF ADAPTATION DIRECTION WAS NOT CHANGED, TRY ANOTHER DIRECTION |

IF NO SAMPLE POINT WAS MODIFIED
⇒ REDUCE STEP WIDTH

REPEAT OPTIMIZATION FOR ALL COORDINATES UNTIL ABORT CRITERION IS MET
(STEP WIDTH = 1 AND NO IMPROVEMENT CAN BE ACHIEVED)

ADAPTIVE OPTIMIZATION PROCESS FOR ULTRASONIC MEASUREMENT SIGNALS

BACKGROUND OF THE INVENTION

1. Field of the Invention

The invention is directed to a method for the adaptive optimization of ultrasound measurement signals.

2. Description of the Prior Art

The measuring precision and the structural resolution of ultrasound pulse-echo systems is critically determined by the spectral system bandwidth and by the chronological shape of the measurement signal. For example, pulse-shaped measurement signals with a broad frequency response and optimally short build-up and decay times are desirable for a high measuring precision and good axial resolution. In standard ultrasound transducers, it is usually a matter of weakly attenuated, resonant transducers that preferably oscillate at specific modes and, due to their mismatch to the acoustic medium of air, exhibit a limited efficiency/bandwidth product. For this reason, a pulse-shaped excitation of these transducers does not as a rule lead to measurement signals that are optimum in the above sense.

The, reprint from Fachberichte Hüttenpraxis Metall-Weiterverarbeitung. volume 19, No. 2, 1981, H. A. Crostak, "Grundlagen des CS-Technik", discloses a possibility for improving the transmission signal of an ultrasound transducer for materials' testing with ultrasound. This ensues by the variation of the frequency spectrum of the transmission signal, for example by multiplication of a pulse by one or more selected functions.

It is fundamentally possible to partially compensate the non-ideal transmission properties of the transducers with a suitable filtering. What are referred to as inverse filters can be applied in the field of ultrasound technology in order to improve the characteristic data of ultrasound measurement systems.

Such an inverse filter is disclosed in, Sedki M. Riad, "The Deconvolution Problem: An Overview", IEEE, 1986. This is thereby a matter of a post-filtering.

In inverse filtering, the ultrasound signal output by a transmission transducer is received and subsequently charged with the inverse transfer function of the system.

A further possibility is to calculate an inverse filter function into the signal to be transmitted. This represents an inverse pre-filtering.

Given post-filtering, the reception signals must be filtered after every measurement. Since analog variable filter can be realized only with great difficulty, this filtering usually ensues with digital filters, whereby implementing the filtering in real time is partly possible only with relatively great outlay.

One disadvantage of inverse pre-filtering is the need for a linear, broadband power transmission amplifier for the excitation of the ultrasound transducer. Due to the great outlay and the relatively high power consumption, the use thereof is often unacceptable, particularly given reasonably priced "stand alone" apparatus.

Both inverse pre-filtering as well as post-filtering have the disadvantage that information about the overall system is necessary for the calculation of the inverse filter, these having to be present in advance, and the method very easily becoming unstable when these information are not considered or given imprecise data and/or optimum results cannot be achieved.

SUMMARY OF THE INVENTION

An object of the present invention is to provide a method for the adaptive optimization of an ultrasound signal output by an ultrasound transducer, whereby no advance information about the overall system need be present. Further, the method should also be suitable for non-linear systems.

The above object in accordance with the principles of the present invention in a method for adaptive optimization of ultrasound measurement signals wherein an ultrasound transducer is excited with a transmission signal, thereby causing an ultrasound signal to be emitted and a reflected ultrasound signal to be received, an error value is formed from features of the received ultrasound signal, the signal curve of the transmission signal is then modified in sections or segments, and a resulting modified ultrasound signal is emitted and received, and an error value for this received ultrasound signal is also obtained, the transmission signal is updated if this latest error value is less than or equal to the previous error value, and the step of modifying the transmission signal in sections is implemented again if the error value has become larger. These steps are then repeated for all sections of the signal curve for the transmission signal, until the entire signal curve has been modified, where necessary.

The method has the advantage of always leading to a stable, optimizing solution regardless of the system transmission properties.

The method has the additional advantage that the probability of achieving a sub-optimum result with a high error value is low. Further, complicated hardware and software can be foregone as a result of the inventive method.

DESCRIPTION OF THE PREFERRED EMBODIMENTS

Figure 1:
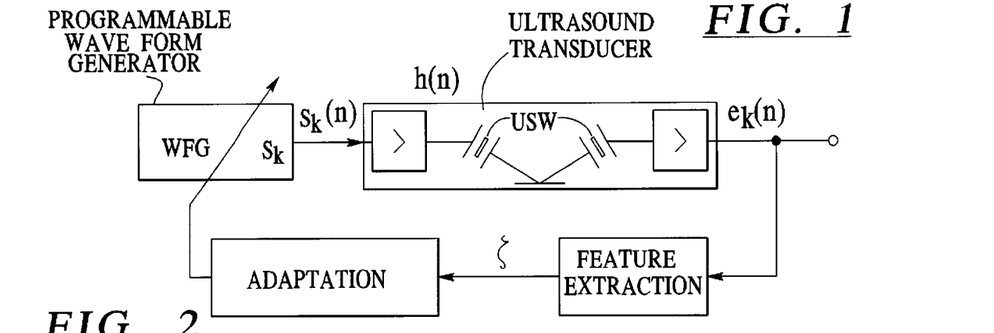
FIG. 1 is a block diagram of a system for adaptive optimization of ultrasound measurement signals, operating in accordance with the inventive method.

The underlying measurement installation for generating an optimized ultrasound signal is shown in FIG. 1. An arbitrary transmission signal $s_k(n)$ with limited temporal length and amplitude discretization can be generated with a freely programmable waveform generator WFG. The transmission signal $s_k(n)$ generated in this way is transmitted via an ultrasound transducer USW and is received at the same ultrasound transducer or an a different ultrasound transducer USW. Error features $\zeta$, also referred to only as features below, are derived from the reception signal $e_k(n)$. These are utilized in the optimization procedure for evaluating the reception signal $e_k(n)$ and for calculating the new transmission signal $s_k(n)$. The reception signal $e_k(n)$ is derived from the convolution of the transmission signal $s_k(n)$ with the pulse response (=transfer function) $h(n)$ of the overall system GS. $e_k(n) = s_k(n) * h(n)$.

The transmission signal vector $s_k$ is derived as:

$s_k = (s_{k1}, s_{k2}, \ldots, s_{kn}, s_{kn+1}, \ldots, s_{kN})$ $1 \leq n \leq N$ n=index for the $n^{th}$ sample of the transmission signal
k=index for the $k^{th}$ transmission signal.

The error features $\zeta$ on the basis whereof the optimization is undertaken are derived from the reception signal $e_k(n)$. The overall error function $\zeta(s_k)$ is a function of the features $\zeta$ and, thus, a function of the transmission signal vector $s_k$.

$\zeta(s_k) = f(s_{k1}, s_{k2}, \ldots, s_{kN})$

The shape of the error curve derives from the transfer function $h(n)$ and the selected features $\zeta$. The signal optimization ensues in that the transmission signal vector $s_k$ is modified such that the value of the error function $\zeta(s_k)$ becomes optimally minimal. This is an N-dimensional optimization problem whose complexity is dependent on from the properties of the error curve.

Figure 2:
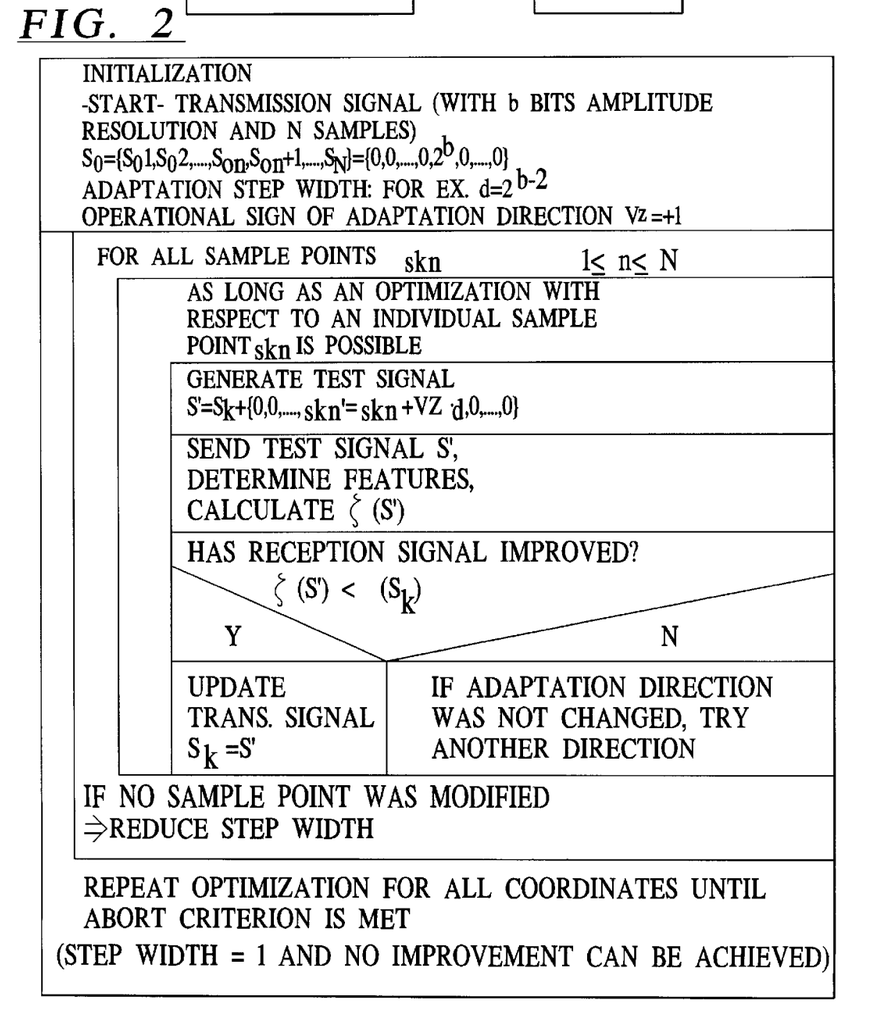
FIG. 2 illustrates the basic steps of the inventive method.

FIG. 2 shows the flowchart of the optimization method. Proceeding from a delta pulse as initialization signal, one successively proceeds in the N-coordinate directions by a fixed step width d, so that the error features are minimized with respect to the individual coordinates. One starts with a step width d that is half as big as the maximally adjustable amplitude value of the transmission samples. When an improvement cannot be achieved at any coordinate with the given step width d, then the step width is made smaller by the factor 2 and the optimization procedure is repeated for all coordinates. The abort criterion of the method is met when an improvement can no longer be achieved with a step width d=1, which represents the smallest step width.

The very big step widths at the beginning of the method have a positive influence to the effect that it is thereby improbable that the method will proceed into a flat local minimum, a sub-optimum solution, with an extremely high error level and stagnate there.

Figure 3:
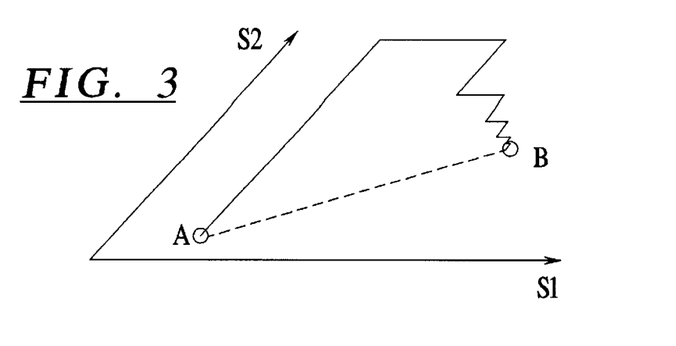
FIG. 3 is a schematic illustration of a typical search path using the coordinate search technique, which can be implemented in conjunction with the inventive method.

Let it be noted that it would not be meaningful to determine the error minimums very exactly in small steps with respect to a coordinate at the beginning of the adaption since the individual coordinates do not reside orthogonally relative to one another and, thus, the optimum value of a coordinate is dependent on all others. Consequently, an exact optimization of an individual coordinate value is only meaningful when all other coordinates have also been optimized relatively well. This behavior can be illustrated in a two-dimensional, non-orthogonal space, as shown in FIG. 3. The search begins in point A and proceeds in the direction point B, whereby successive advances are made in one of the two directions S1 or, respectively, S2 in alternation. The error value is derived from the respective distance of the momentary position from the point B.

It can also be seen from FIG. 3 that the search method is fundamentally stable and converges toward the absolute minimum given a unimodal function. The broken line entered in FIG. 3 represents the direct path between the start point A and the target point B.

As in all currently known multi-dimensional optimization methods, it can also not be precluded in the coordinate search method used for ultrasound signal optimization that the algorithm, given non-unimodal functions, converges in a sub-optimum local minimum of the error function $\zeta(s_k)$ and not in the absolute minimum. In order to clearly reduce the probability of a poor, sub-optimum solution, it is possible to additionally overlay the reception signal with a noise signal, so that there is a statistical possibility of "jumping out" of sub-optimum minimums and thus proceeding to a more deeply placed error level. Given this principle, the overlaid noise power is successively reduced after every adaption cycle over given a stagnating learning result. A method having a comparable basic idea for multi-dimensional optimization was presented by S. Kirkpatrick, C. D. Gelatt, M. P. Vecchi, "Optimization by Simulated Annealing," Science, Vol. 220, pp. 671–680, May 1983, under the name "Simulated Annealing". Since ultrasound measurement signals are generally overlaid by noise quantities, the signal-to-noise ratio of the reception signal can be very simply achieved in practice via an increase or reduction of the transmission voltage or averagings over a plurality of measuring cycles. Given a digitalized processing of the reception signals, noise quantities can be computationally added up over and above this.

Figure 4:
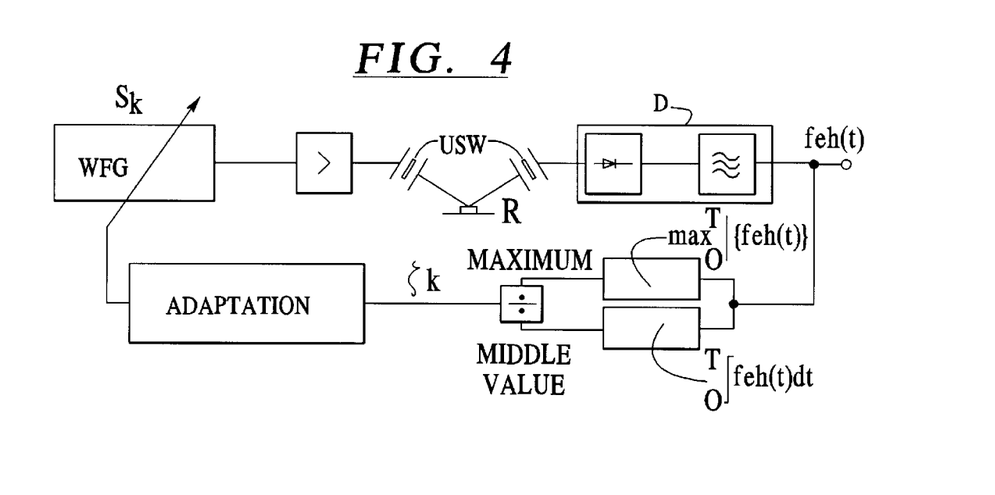
FIG. 4 is a block diagram of a further embodiment of a system for implementing the inventive method, for adaptive optimization of envelope signals.

The method was tested in practice on the basis of the envelope signal of the air ultrasound measurement system, see FIG. 4. The entire concept of the investigated, adaptive optimizer is shown there. A transmission signal $f_s(t)$ is generated with a freely programmable waveform generator WFG and beamed out via an ultrasound transducer USW. The signal reflected at a reflector R is received by the same ultrasound transducer or by a different ultrasound transducer USW. The envelope signal $f_{eh}(t)$ is acquired from the reception signal with a demodulator D. The low-frequency envelope signal $f_{eh}(t)$ was evaluated and not the high-frequency time signal; this, however, would be possible in the same way. The square of the relationship of the area under the envelope, which is proportional to the average value of the voltage amplitudes, and the amplitude maximum was employed as error criterion:

$$\zeta = \left( \frac{\int_0^T f_{eh}(t)dt}{\max\limits_0 |\{f_{eh}(t)\}|} \right)^2$$

whereby T is the time duration for a single measurement cycle.

A low error value $\zeta$ thus arises given a reception signal with a narrow, high major oscillation and small minor oscillations. The best signal, accordingly, would be a delta pulse with the error value of 1. The advantage of this error criterion is comprised therein that the two features, amplitude peak value and average value, can also, as warranted, be determined very easily with simple operational amplifier circuits. When the error features are determined with hardware, then the time signal need no longer be digitized; the two features merely have to be sampled once per transmission event, as a result whereof the hardware outlay and the processing time are clearly reduced.

Figure 5A:
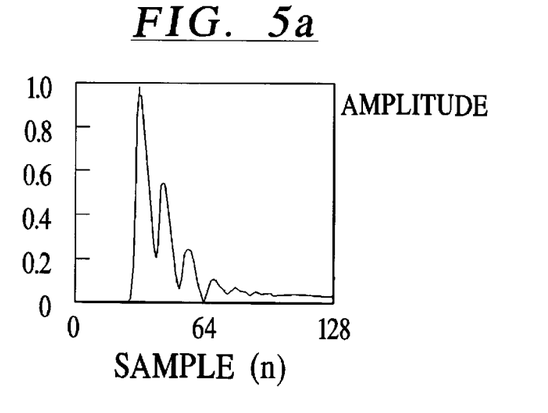
FIG. 5a shows the envelope of a typical pulse response.
Figure 5B:
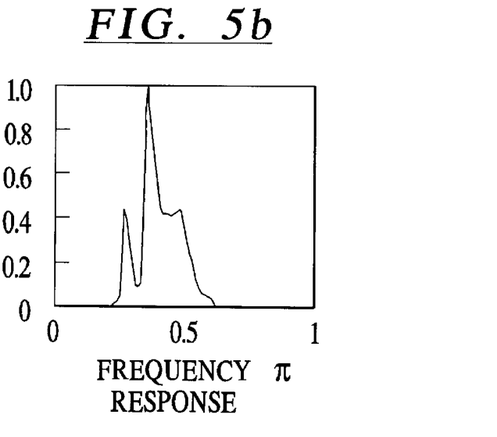
FIG. 5b shows the associated system frequency response.

The ultrasound transducer employed is a conventional piezoceramic, operable in the radial thickness mode, resonator, operable in the radical thickness mode, with $\lambda/4$ matching layer. The relative 3 dB bandwidth of the transducer (3 dB bandwidth centered on the center frequency) lies at approximately 0.1. The overall system pulse response is determined almost exclusively by the transducer transmission properties. The envelope of the system pulse response and the appertaining frequency response are shown in FIG. 5.

Figure 6A:
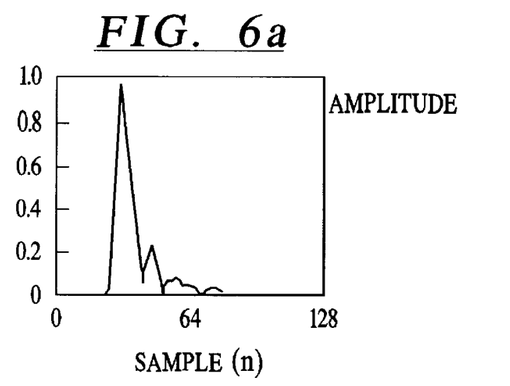
FIG. 6a shows the envelope of a typical reception signal after an adaptation cycle.
Figure 6B:
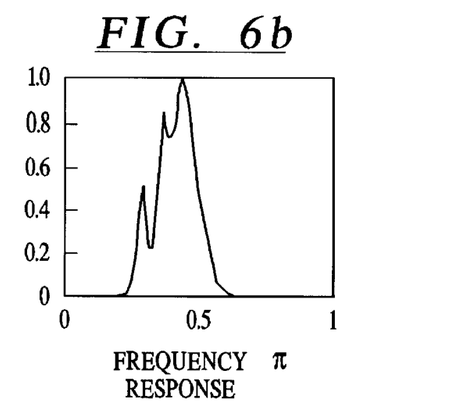
FIG. 6b shows the associated system frequency response.

An optimized transmission signal with 128 samples and 8-bit quantizing was generated for the illustrated system. Two optimization stages of the adaption are recited in FIGS. 6 and 7. FIG. 6 shows the envelope and the frequency response of the reception signal after the first adaption cycle; here, thus, all transmission samples have been optimized once with the very big initial step width.

Figure 7A:
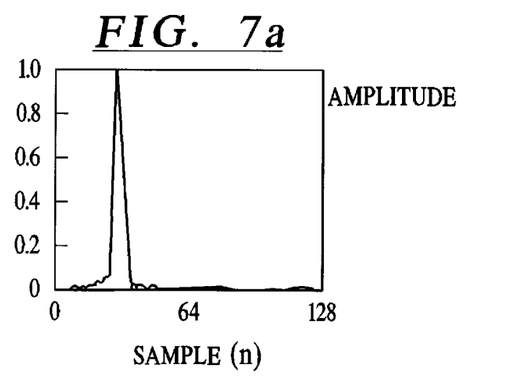
FIG. 7a shows the envelope after a number of adaptation cycles.
Figure 7B:
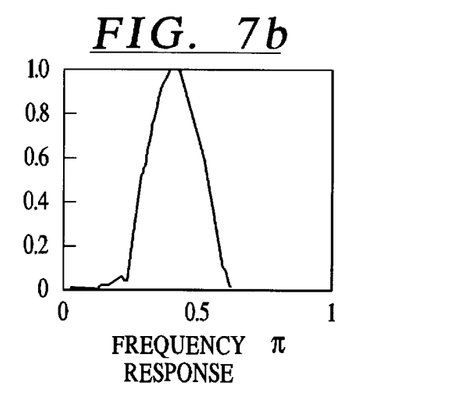
FIG. 7b shows the associated frequency response.

FIG. 7 shows the final result of the optimization after 36 cycles. One can see in the envelope of the reception signal that the minor oscillations have been suppressed to the farthest-reaching extent; the reception signal has a smooth curve and its shape is very similar to a Hanning window. Compared to the normal pulse response, the 3 dB bandwidth has enlarged by approximately the factor 5.

Figure 8A:
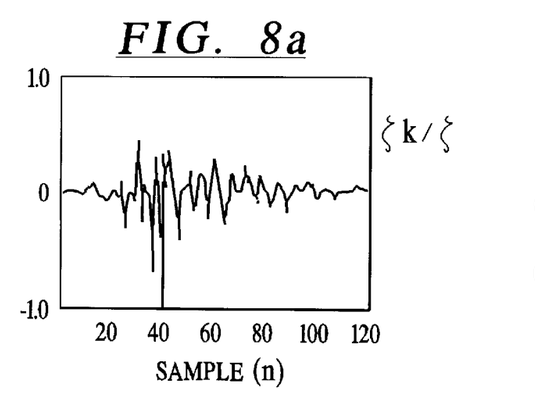
FIG. 8a shows the optimized transmission signal after completion of the inventive method.

The example shows that an adapted transmission signal as shown in FIG. 8a can be generated that leads to a clearly improved reception signal and that is very well-suited for further signal evaluation.

Figure 8B:
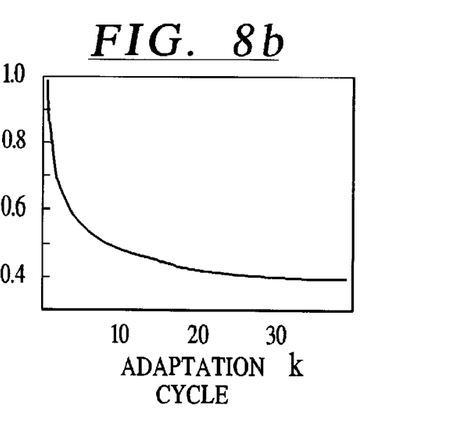
FIG. 8b shows the associated error curve.

The convergence properties of the method can be seen on the basis of the error curve that is shown in FIG. 8b. The development of the error value dependent on the plurality of adaption cycles is shown. The curve is also referred to as learning curve. The error diminishes very fast in the first adaption cycles and then converges relatively slowly (hyperbolically) toward the minimal final value. The abort criterion is met here after 36 cycles.

The error function is usually not a matter of a unimodal function. Both the overall function as well as the error functions of the individual transmission samples can have several minimums. A typical function of the error dependent on the value of an individual transmission sample is shown in FIG. 9.

Figure 10:
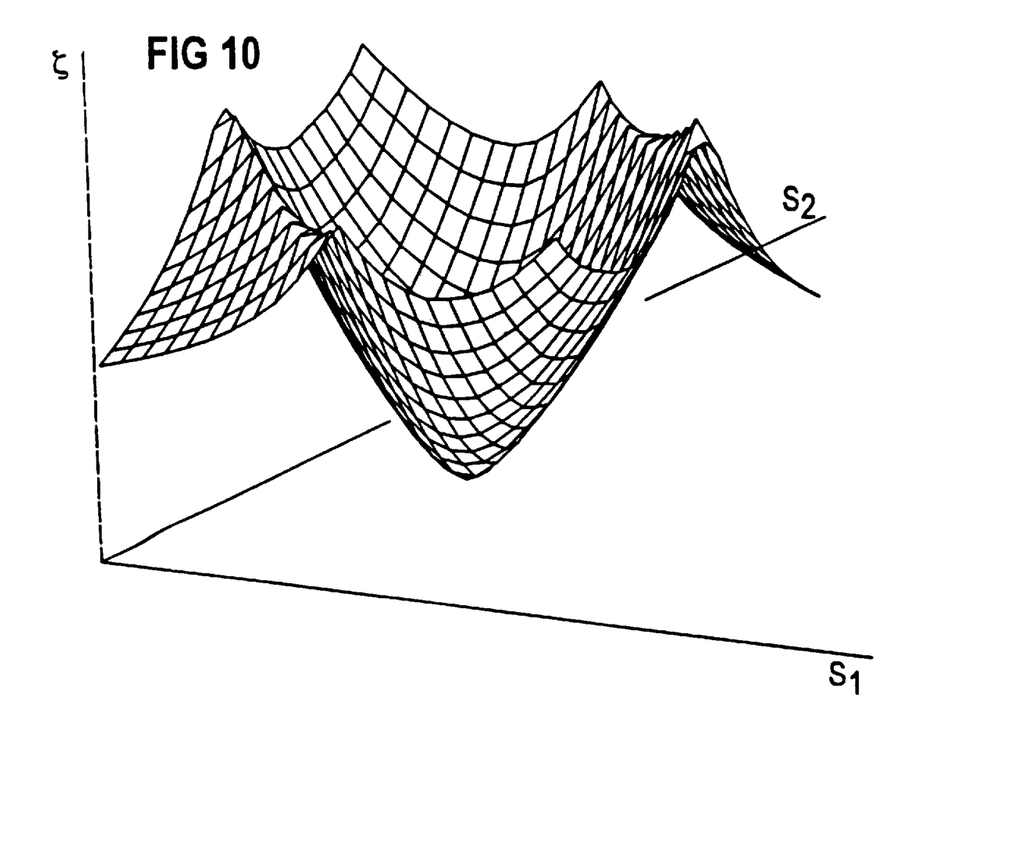
FIG. 10 illustrates an error function employed in the inventive method, dependent on two samples.

FIG. 10 shows an error function dependent on two transmission samples. In addition to the pronounced global minimum, several local minimums can be seen in the edge regions of the function. In addition to the fact that the overall error function is composed of the individual error functions, the fact that the error function of individual transmission samples can have a plurality of minimums is of significance particularly because the entire optimization proceeds via the sub-optimizations in the individual coordinate directions.

Figure 9:
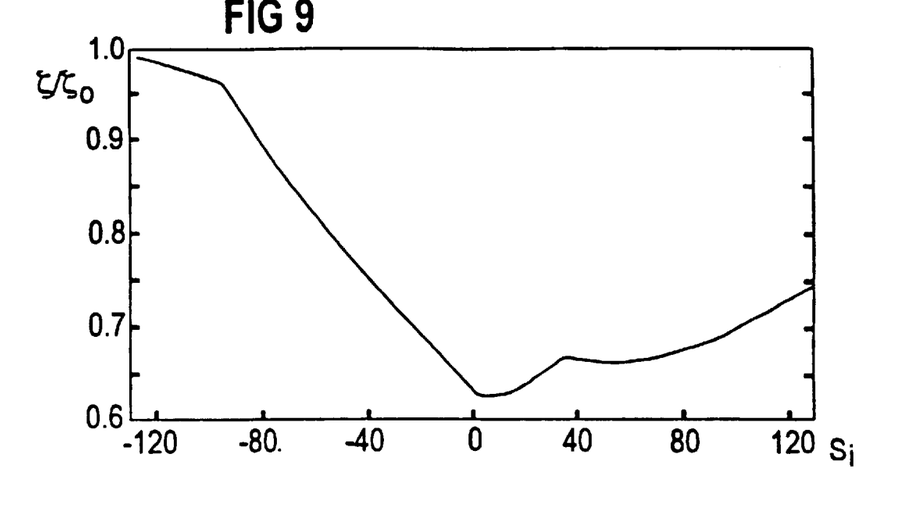
FIG. 9 illustrates a typical error function for an individual sample employed in the inventive method.

It should be noted that FIGS. 9 and 10 show typical error functions only for the beginning of the adaption. When the optimization has advanced rather far in the direction of the minimum, then all error functions of the individual transmission samples are quadratic functions (parabolas).

Figure 11:
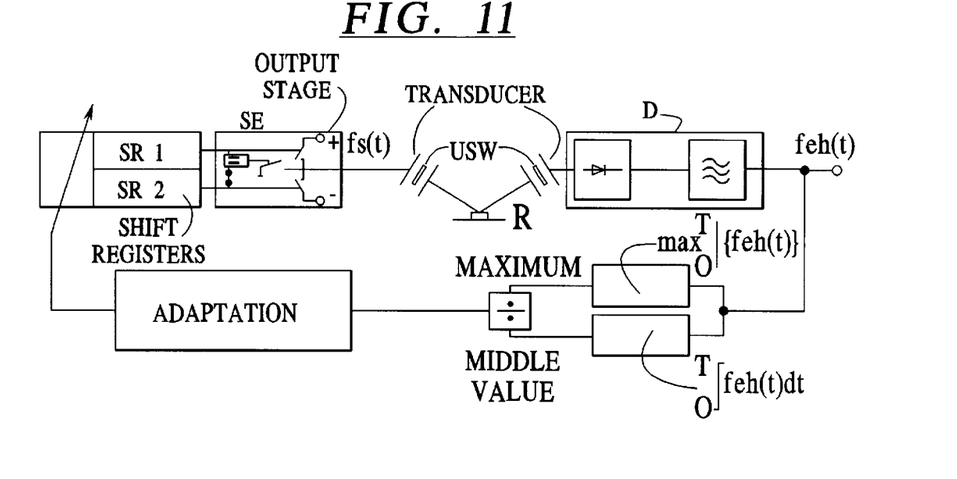
FIG. 11 is a block circuit diagram for adaptive optimization in accordance with the inventive method by pulse excitation.

FIG. 11 shows another application of the method. A transmission signal comprising 32 samples was quantized in three stages. Positive voltage pulse, negative voltage pulse and neutral potential. The pulse series that control the switched output stage SE can, for example, be generated by two shift registers SR1 and SR2 that are loaded with the corresponding values before the transmission event. The optimization method was correspondingly matched to the three-stage quantization stage.

Figure 12A:
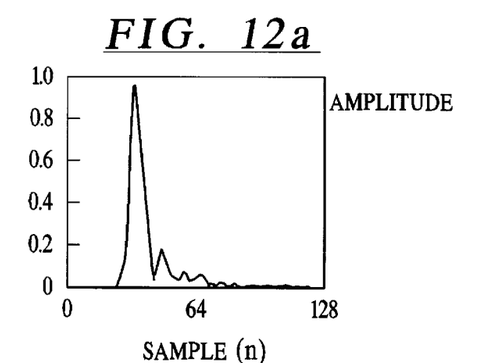
FIG. 12a shows an optimized reception signal given three-stage quantization of the transmission signal.
Figure 12B:
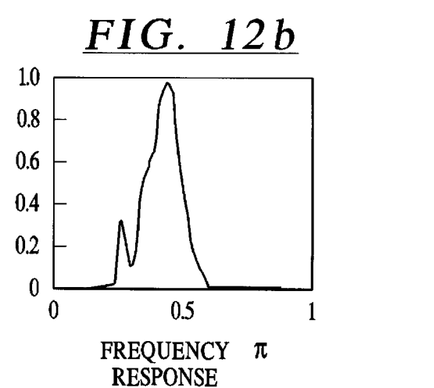
FIG. 12b shows the associated frequency response.
Figure 13:
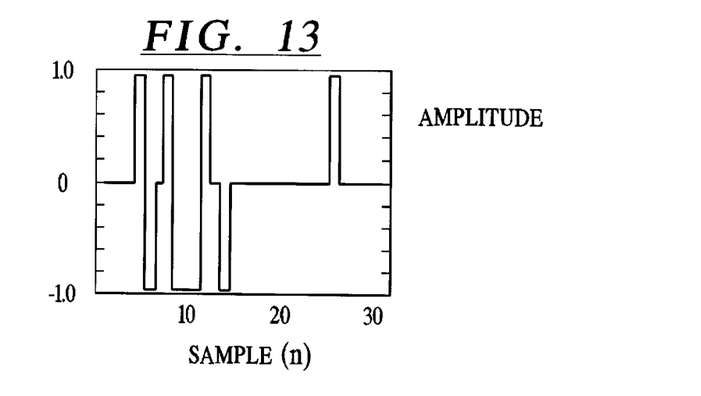
FIG. 13 illustrates the optimized transmission signal given three quantization stages.
Figure 14A:
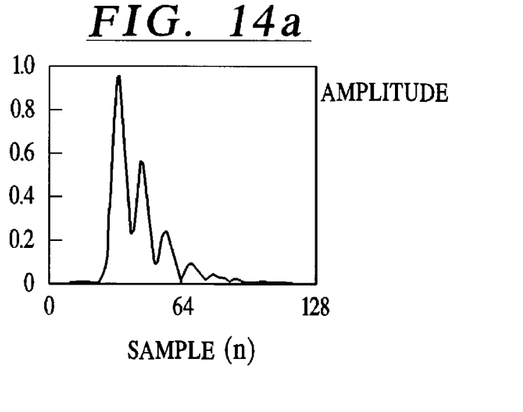
FIG. 14a shows a simulated response which produces a zero point in the frequency response.
Figure 14B:
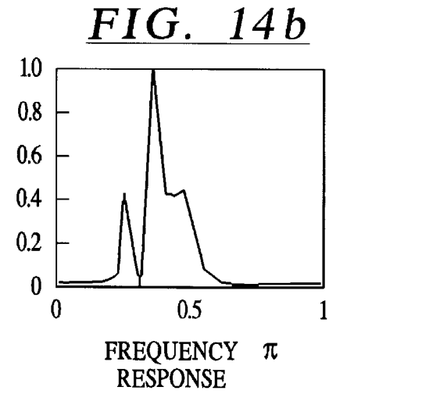
FIG. 14b shows the associated frequency response.
Figure 15A:
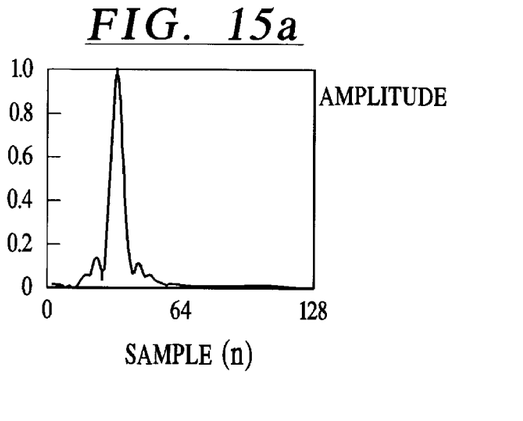
FIG. 15a shows an optimization result for a system operated in accordance with the inventive method, and simulated according to FIG. 14a, and FIG. 15b shows the associated frequency response.
Figure 15B:
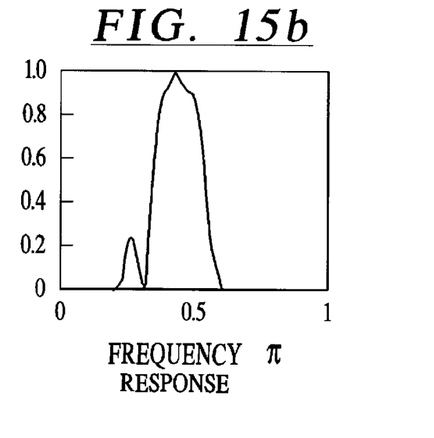

As the result of the adaptation, see FIG. 12, it becomes clear that a noticeable optimization of the reception signal, see FIG. 14, can also be achieved given this simple transmission signal that is shown in FIG. 13. The minor oscillations in the envelope are greatly reduced and the signal bandwidth has enlarged by about the factor 2 compared to the pulse response.

Such a transmission circuit working nearly without losses can be combined with an ultrasound transducer in a hybrid arrangement in order to thus obtain improved measurement signals with a higher signal-to-noise ratio, shorter build-up and decay times and/or broader frequency response, this, for technically physical reasons, having been unobtainable with a normal ultrasound transducer or only obtainable with great outlay.

The inventive method is also suitable for air-ultrasound transducer arrays since the complicated analog push-pull output stages can be replaced by an integrated array switched output stage.

In addition to the described optimization of the axial resolution, other criteria can also be of interest, for instance an optimally short transiency of the first oscillation of the received ultrasound signal. An optimally steep build-up edge leads to a high precision in a signal evaluation with an analog comparator circuit. Features for the evaluation of these properties are, for example, the height of the first maximum $h_1$ in the received ultrasound signal and the slope $m_1$ of the chronologically preceding signal curve. The error value $\zeta$ is calculated, for example, as:

$$\zeta_s = \left( \frac{1}{h_1 \cdot m_1} \right)$$

When minor oscillations are to be additionally compensated, then the error features $\zeta$ and $\zeta_s$ can be combined to an error value $\zeta_k$:

$$\zeta_k = \left( \frac{\int_0^T f_{eh}(t)dt}{h_1 \cdot m_1} \right)^2$$

In a certain sense, the rough signal quantization represents a non-linearity of the system. It is thus clear that highly non-linear systems can also be optimized with the method. By contrast to a direct calculation of an inverse filter, whereby the linear signal transmission is a prerequisite, only extremely low demands are to be made of the linearity of the transmission elements such as, for example, transmission and reception amplifier in the feature-supported, adaptive signal optimization as realized by the inventive method, as a result whereof the hardware can be significantly simplified.

The robustness of the inventive method becomes clear with reference to another example. This is thereby a matter of the simulation of a system that exhibits a $0^{th}$ in the frequency response and can thus not be directly inverted. The signal curve of the simulated system corresponds to that of FIG. 5, whereby the glitch in the signal spectrum was replaced here by a true zero point, see FIG. 14. A comparable spectrum could derive, for example, for an ultrasound transducer that oscillates weakly attenuated on various modes and the signal energy in the spectral range between the modes is therefore disappearingly small. As a result of the feature-supported optimization, see FIG. 15, it is clear that the generation of an adapted signal succeeds unproblematically here.

The robustness of the method arises from the fact that the behavior of the overall system is controlled during the adaption. A durable modification of the filter function only occurs when the error features that arise from the complete reception signal diminish and the behavior of the system, thus, has improved. It is thus precluded from the very outset that the method becomes unstable, namely dependent on the system to be optimized, whereby this can be non-linear, weakly non-stationary and "ill-posed".

A further advantage of the inventive method is also to be seen therein that no causality considerations whatsoever are needed for the calculation of the inverse signal since the extracted error signals are independent of running time and only the shape of the reception signal is optimized. Dead times therefore need not be considered.

The adaption speed is critically determined by the time that is required for a transmission event dependent on the transit time of sound. The time that the method requires for the calculation can be neglected since only a few, extremely simple operations have to be implemented.

The method is suited for an implementation on an economical micro-controller since only very little computing power is required.

Figure 16:
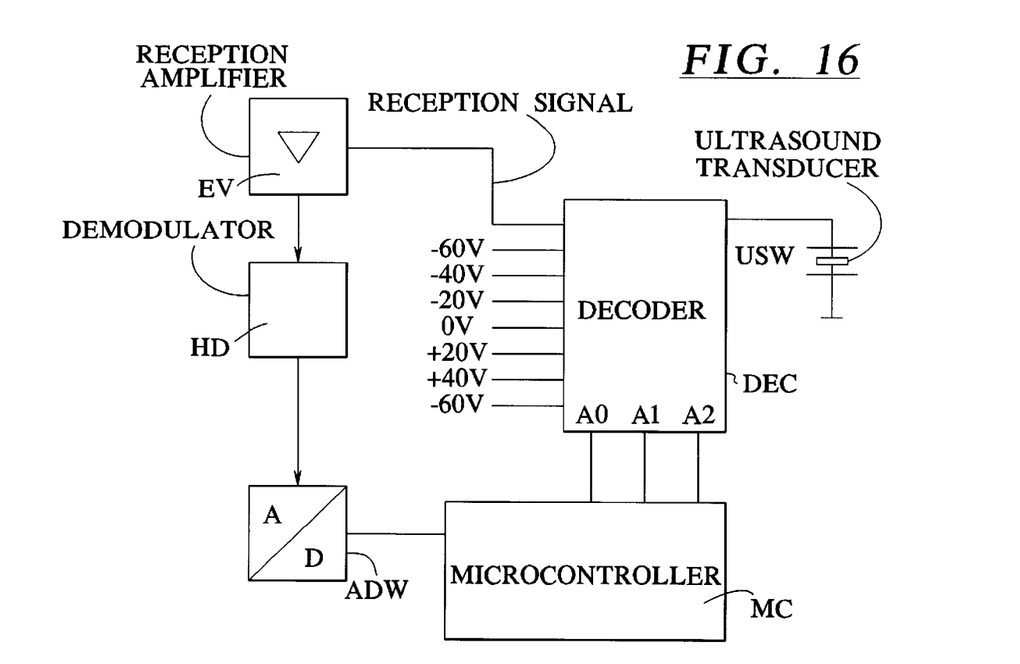
FIG. 16 is a circuit diagram of a first embodiment of a circuit composed of components for implementing the inventive method.

The circuit arrangement according to FIG. 16 is suitable for the inventive method. It includes a 1-of-8 decoder DEC, for example Silikonix HV15C, that has its input side occupied with various voltages between −60 and +60 V. These are applied to the output of the decoder DEC, to which the ultrasound transducer USW is connected, by the control signals applied to the control addresses A0, A1, A2 that are generated in and supplied from the micro-controller MC. The ultrasound signal reflected from a subject is received via the ultrasound transducer USW and supplied to the reception amplifier EV via the decoder DEC. An envelope signal is formed from the amplified reception signal with an envelope demodulator HD, this envelope signal being supplied to an analog-to-digital converter ADW that forwards the digitized envelope signal to the micro-controller MC. The method for the adaptive optimization is implemented in the micro-controller MC.

Figure 17:
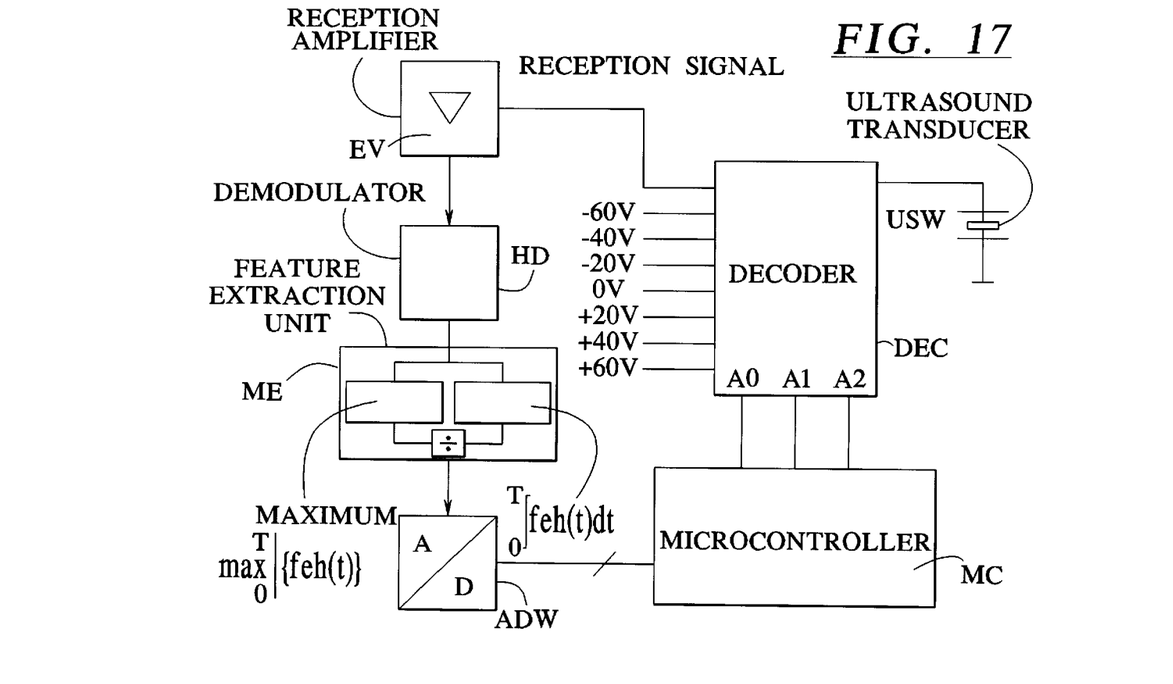
FIG. 17 is a circuit diagram of a second embodiment of a circuit composed of components for implementing the inventive method.

The circuit arrangement shown in FIG. 17 deviates from that shown in FIG. 16 insofar as the feature extraction is not implemented in the micro-controller MC but instead in a unit for feature extraction ME that precedes the analog-to-digital converter ADW.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for adaptively optimizing an ultrasound measurement signal emitted by an ultrasound transducer, comprising the steps of:
    (a) exciting a transmitting ultrasound transducer with a transmission signal, said transmission signal exhibiting a signal curve comprising a plurality of successive sections, and thereby causing said transmitting ultrasound transducer to emit an emitted ultrasound signal which produces a reflected ultrasound signal;
    (b) receiving said reflected ultrasound signal with a reception ultrasound transducer as a received ultrasound signal, said received ultrasound signal having at least one feature representing a deviation of said emitted ultrasound signal from a predetermined optimum signal;
    (c) evaluating said received ultrasound signal to obtain an initial error value dependent on said at least one feature;
    (d) modifying a section of said transmission curve to obtain a modified transmission curve and exciting said transmission ultrasound transducer with said modified transmission curve to emit a new emitted ultrasound signal, which produces a new reflected ultrasound signal;
    (e) receiving said new reflected ultrasound signal as a new received ultrasound signal, said new received ultrasound signal also having said at least one feature;
    (f) evaluating said new received ultrasound signal to obtain a new error value dependent on said at least one feature in said new received ultrasound signal;
    (g) comparing said initial error value and said new error value and updating said transmission signal if said new error value is less than or equal to said initial error value, and repeating steps (d), (e) and (f) for said section if said new error value is larger than said initial error value; and
    (h) repeating steps (d) through (g) for all of said sections.

2. A method as claimed in claim 1 comprising the additional step of using a single ultrasound transducer as said transmitting ultrasound transducer and as said reception ultrasound transducer.

3. A method as claimed in claim 1 wherein step (d) comprises modifying a section of said transmission curve in successively smaller steps until a step width falls below a predetermined threshold.

4. A method as claimed in claim 1 wherein steps (b) and (e) are further defined by using an area defined by an envelope respectively of said received ultrasound signal and said new received ultrasound signal, as said feature.

5. A method as claimed in claim 1 wherein steps (b) and (e) are further defined by using an amplitude maximum respectively of said received ultrasound signal and said new received ultrasound signal, as said feature.

6. A method as claimed in claim 5 wherein step (c) is further defined by forming said initial error value as a quotient of an area defined by an envelope of said received ultrasound signal and said amplitude maximum of said received ultrasound signal, and wherein step (f) is further defined by forming said new error value as a quotient of an area defined by an envelope of said new received ultrasound signal and said amplitude maximum of said new received ultrasound signal.

7. A method as claimed in claim 1 wherein steps (b) and (e) are further defined by using a slope of a signal excerpt respectively of said received ultrasound signal and said new received ultrasound signal as said feature, for optimizing build-up time of said emitted ultrasound signal.

8. A method as claimed in claim 1 wherein steps (b) and (e) are further defined by using an amplitude maximum respectively of said received ultrasound signal and said new received ultrasound signal as said feature, for optimizing build-up time of said emitted ultrasound signal.

9. A method as claimed in claim 8 wherein step (b) is further defined by forming said initial error value as a reciprocal of a product of said amplitude of said received ultrasound signal and a slope of a signal excerpt of said received ultrasound signal, and wherein step (f) comprises forming said new error value as a reciprocal of a product of said amplitude of said new received ultrasound signal and a slope of a signal excerpt of said new received ultrasound signal.

10. A method as claimed in claim 1 comprising the additional step of overlaying said transmission signal with white noise having a noise power, and reducing said noise power of said white noise for each repetition of steps (d), (e) and (f) in step (g).

11. A method as claimed in claim 1 comprising the additional step of discretizing said received ultrasound signal and said new received ultrasound signal.

12. A method as claimed in claim 1 comprising the additional step of forming an envelope of said received ultrasound signal and said new received ultrasound signal.

* * * * *